United States Patent [19]

Engelke et al.

[11] Patent Number: Plant 7,539

[45] Date of Patent: May 28, 1991

[54] PRAIRIE BUFFALOGRASS

[75] Inventors: Milton C. Engelke, Richardson; Virginia G. Lehman, Plano, both of Tex.

[73] Assignee: Texas A & M University System, College Station, Tex.

[21] Appl. No.: 456,851

[22] Filed: Dec. 22, 1989

[51] Int. Cl.[5] ..... A01H 5/00

[52] U.S. Cl. ..... Plt./88

[58] Field of Search ..... 800/200, DIG. 55; Plt./88

[56] References Cited

PUBLICATIONS

Musser, H. B., "Buffalograss" *Turf Management* McGraw-Hill, New York, 1962, p. 97.

Gould, F. W. et al, "77. Buchloe Engelm" *The Grasses of Texas*, 1975 Texas A&M Univ. Press, College Sta., Tex., pp. 355-357.

*Buchlow dactyloides* (Nutt.) Engelm., buffalograss, pp. 38-39, Grass Varieties in the United States, Agriculture Handbook 170, U.S. Department of Agriculture (1959).

Hickey et al., Evaluation of quality in Tall Fescue Turf Trails, pp. 56-62, P. R. No. 4276 (1984).

Beard, J. B., Turfgrass Science and Culture, Prentice-Hall, Englewood Cliffs, N.J. (1973).

Voigt et al, Registration of Texoka Buffalograss, vol. 14, p. 885, Crop Science (Nov.-Dec. 1975).

*Primary Examiner*—James R. Feyrer

*Attorney, Agent, or Firm*—Arnold, White & Durkee

[57] ABSTRACT

A vegetatively reproduced perennial buffalograss cultivar having 2n=40 chromosomes, named "Prairie", particularly distinguished by its rapid spreading stolons, competitive growth, short height, frost and drought tolerance, durability, low maintenance requirements, uniform color and density, and improved turf performance.

3 Drawing Sheets

BACKGROUND OF THE INVENTION

Buffalograss, *Buchloe dactyloides* (Nutt.) Engelm., is a warm-season, stoloniferous, sod-forming, perennial grass. Drought resistant, adapted to grazing, and helpful in erosion control of heavy soils, buffalograss is an important range grass found mainly in the central prairies of the United States with its full range of distribution extending from Canada to Mexico.

The species is well adapted to warm semi-arid and sub-humid regions of the United States. Levels of annual precipitation supporting optimal growth range from 12 to 25 inches.

Buffalograss is moderately dense, fine-leafed, grayish-green, and drought and temperature tolerant. The species survives drought and severe heat by remaining dormant until there is sufficient moisture to sustain growth.

The shallow root system permits this species to take maximum advantage of brief summer rains. When water is supplied, rapid growth occurs. Buffalograss will thus survive without supplemental irrigation, but will more actively grow and hold its green color throughout the season if irrigated.

Buffalograss is a highly adaptable grass which requires little maintenance, and which is highly competitive in adverse conditions. This species is short growing, thus requiring only occasional mowing. Although buffalograss grows best on relatively heavy, fertile, well drained soils, it is adaptable to a wide range of soil conditions. In addition, it has good wear tolerance, and persists under close mowing and intense traffic.

In the past, buffalograss has not been developed specifically for turf purposes. To the contrary, varieties of buffalograss on the market were developed as forage grasses, useful for dryland grazing and vegetation.

Existing varieties of buffalograss such as Texoka, Sharps Improved, and Comanche reproduce sexually from seeds. These grasses were cultivated specifically for forage rather than turf purposes and are produced and distributed predominately by seed. The seeded varieties of buffalograss produce female and male flowers, the latter of which are generally considered unsightly. These buffalograsses also lack uniformity and density because the genetic diversity of seeded buffalograsses results in a highly variable population. In particular, segregated male and female individual plants become obviously distinct within 2 to 3 years and thus create an irregular turf.

Moreover, buffalograss seed is surrounded by a burr which must be pretreated to reduce subsequent dormancy. The burr represents a hard shell around three to four caryopsis which must be pretreated to break dormancy. Germination of the burred seeds is also often erratic and difficult to predict or influence, making uniform stand establishment difficult. In addition, the burr does not flow uniformly through many of the seeders or drills designed for normal grass seeds. Thus, it is difficult to establish existing varieties of buffalograss in a uniform and rapid manner.

SUMMARY OF THE INVENTION

Prairie is distinguished from existing varieties of buffalograss in that it is a vegetatively reproduced female plant having 2n chromosomes equals 40. It is more uniform, shorter, denser, and more competitive. It has more rapid spreading stoloniferous growth habit, greater durability; reduced water, mowing and other maintenance requirements; and improved, uniform color and density. Prairie has a blue green color, fine leaf blade, and short leaf length. These agronomic traits render it particularly suitable for home lawns, recreational areas, and industrial turfs.

BRIEF DESCRIPTION OF THE PHOTOGRAPHS

DETAILED DESCRIPTION OF THE PLANT

Figure 1:
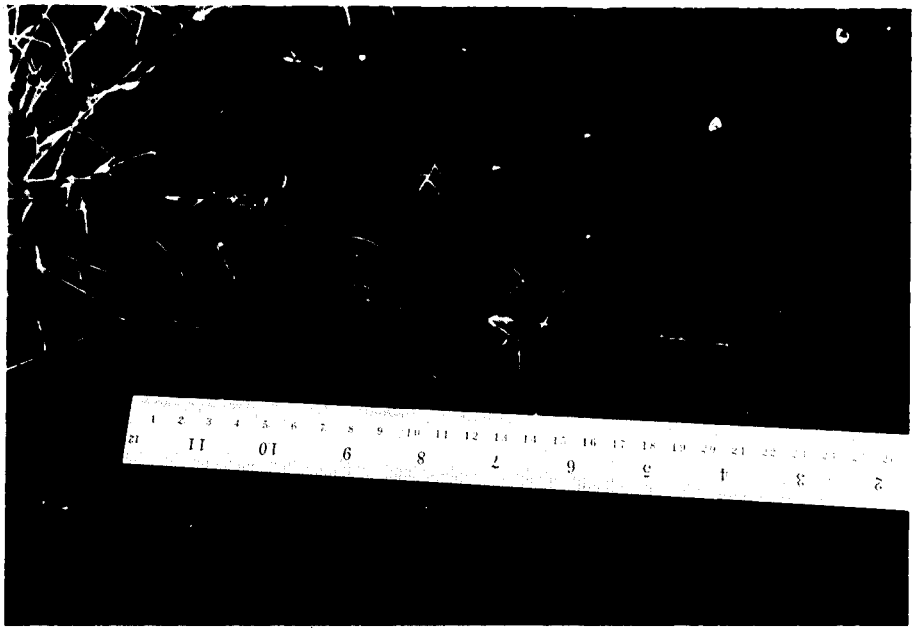
FIG. 1 is a photograph of Prairie of the stolon growth originating from a six weeks old sprig, showing the long internodes, slight pink color hue on the internodes, with profuse branching occurring at the nodes.
Figure 2:
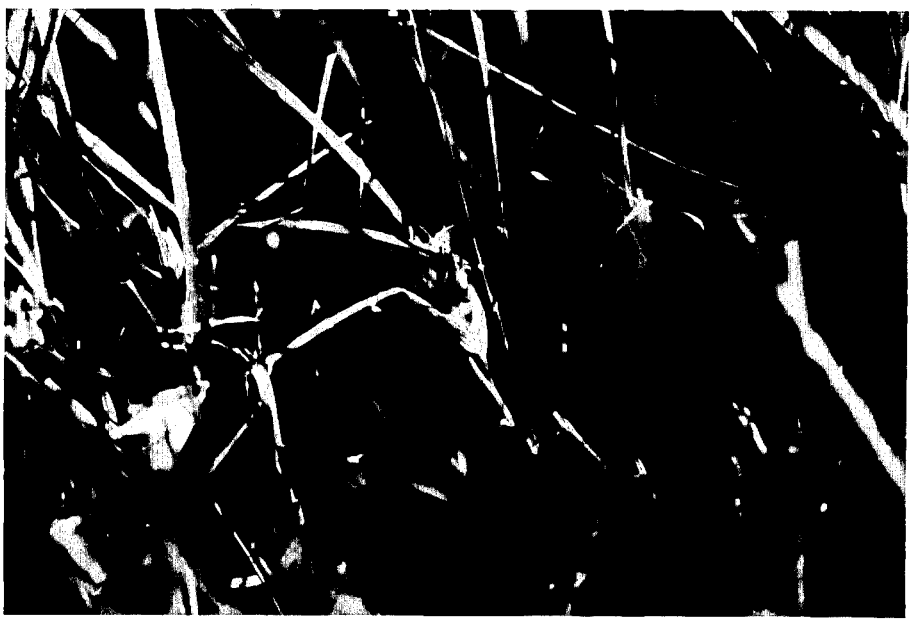
FIG. 2 is a photograph of a pistillate, female, flower or burr of Prairie with light pink stigmas. The burrs are borne within the turf canopy, which is usually hidden, and develop no seed in the absence of a compatible pollen source.
Figure 3:
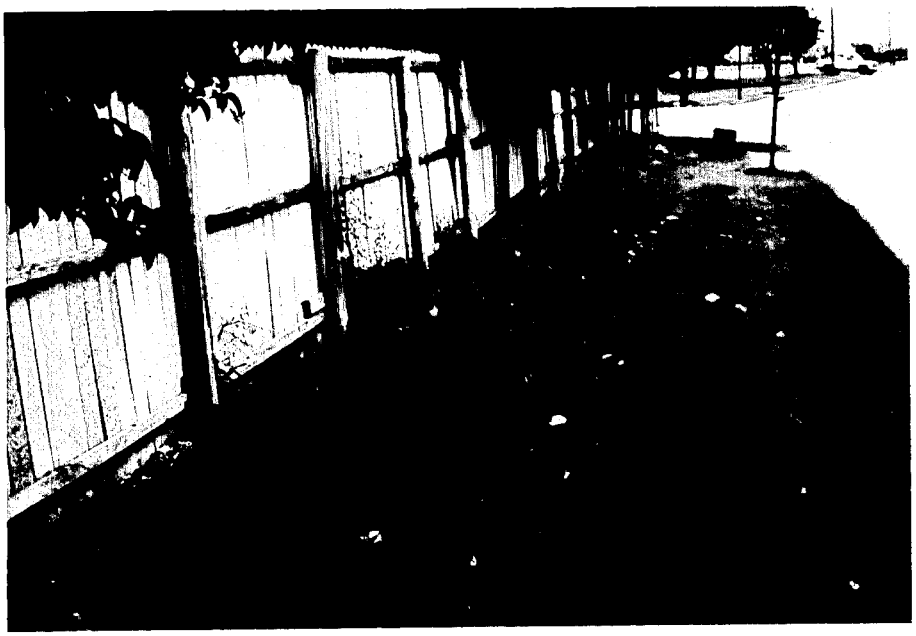
FIG. 3 is a photograph of Prairie established in a high traffic, city parkway. The fence line is chemically controlled to eliminate the necessity of mowing and, as a result, exhibits increased weed growth as compared to the area turfed with Prairie.
Figure 4:
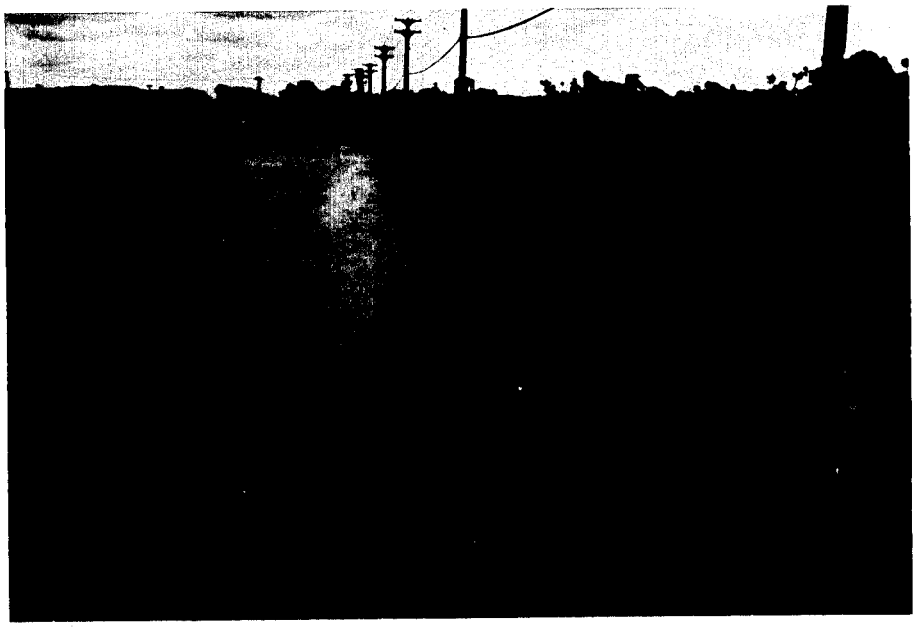
FIG. 4 is a photograph showing the conservation and stabilization of a waterway in an industrial field site using Prairie, established in 1986 from stolons. The area is mowed once annually and neither fertilizer, pesticide, nor irrigation was applied during 1988 and 1989.
Figure 5:
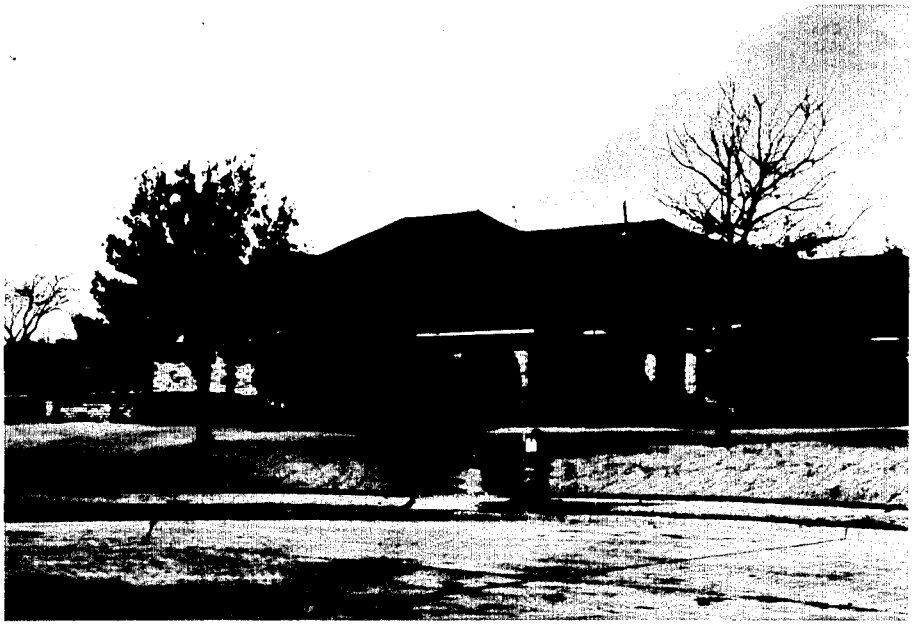
FIG. 5 is a residential lawn of Prairie buffalograss under full winter dormancy, and shows the superior blonde winter color of Prairie as compared to known buffalograsses.

The maternal parent (TAES 1363) of Prairie (TAES 1363.2 or DALBD 8201) was selected from a native grass stand in Falls County, Tex. in 1980. TAES 1363 was included in an open pollinated hybridization nursery with 149 other native accessions. Seed harvested from maternal plant TAES 1363 was germinated and field planted. From this progeny population, a single superior female plant was selected and designated TAES 1363.2 and later DALBD 8201 for advanced field greenhouse and laboratory testing. It was field tested as genotype DALBD 8201 from Corpus Christi, Tex. to Lincoln, Nebr., and from College Station, Tex. to Fort Collins, Colo.

Prairie is particularly adaptable to areas ranging from central and south Texas to the central great plains. It grows best in direct or high sunlight, with performance under shaded conditions comparable to most bermudagrasses.

Prairie may be established by planting sod, sprigs, or plugs. Planting 4 inch prerooted plugs on 12 to 15 inch centers establishes Prairie within 12 to 18 months with little or no supplemental irrigation.

Prairie is a single female plant, which is vegetatively reproduced from stolons, sprigs, plugs, or sod and spreads by stolonization. This variety's rapid stolonization, which facilitates its rapid, even establishment is but one important characteristic distinguishing it from other cultivars of buffalograss.

In contrast to existing varieties of buffalograss, Prairie does not produce male flowers as found with seeded buffalograsses although it produces female flowers prolifically. Nor does it produce viable seed in the absence of a compatible pollen source. Prairie is a dense, fine-leafed, fine-textured, uniform, highly stoloniferous, blue-green turfgrass.

Another significant agronomic improvement of Prairie as compared to known buffalograsses is its shorter height and uniformity in appearance. As a result, Prairie requires substantially less frequent mowing than the other varieties. In the absence of mowing and fertilization, Prairie reaches a mature height of 10 to 15 centimeters under normal management practices. Mature, unmowed plant height depends on fertilization.

In addition, this species is highly durable with excellent cold, heat, and drought tolerance and good to excellent wear tolerance.

Prairie also requires minimal water, nutrition, and other maintenance. As a low growing grass, it requires only infrequent mowing. In addition, Prairie produces minimal biomass, decreasing or eliminating the need for bagging clippings. This cultivar produces a dense uniform sward that crowds out other weeds and undesirable plants. Prairie's aggressive growth characteristics render it far more competitive against weeds than existing varieties.

Thus, a high quality stand of Prairie requires little if any supplemental irrigation or fertilization. This variety requires 60 to 80 percent less water for establishment and maintenance than existing varieties of buffalograss. Prairie is responsive to nitrogen fertilization up to 3 pounds per 100 square feet annually, but will persist with no supplemental fertilization. Fertilization of 1 to 2 pounds of nitrogen per year will improve density of stand, quality of turf, and competitive ability against weed invasion.

In Prairie, aesthetic attributes of density, uniformity, and appealing color are uniquely combined with durability, competitiveness and low maintenance requirements. Together, these agronomic attributes render Prairie particularly suitable for home lawns, recreational areas, such as, for example, golf courses, and industrial parks and for roadside stabilization.

Prairie is more particularly characterized in the following chart and tables, as observed in greenhouse and outdoor testing sites at the Texas Experimental Agricultural Station-Dallas and other locations distributed throughout the central regions of the United States.

The color of Prairie buffalograss is blue green when in season, to yellow, when in dormancy, according to the Royal Horticulture Society Colour Chart ("R.H.S."). Color designations of Prairie in the following chart and tables were assigned according to the R.H.S. Colour Chart, first published in 1966 by The Royal Horticultural Society, London, England.

The Variety

Origin: Cultivar of a single superior female plant originating from the hybridization of a single plant collected from Falls County, Tex. with other native accessions from the Central United States.

Classification:

*Botanic.—Buchloe dactyloides* (Nutt.) Engelm.

Chromosome number: 2n chromosomes=40.

Form: Monocot Gramineae.

Growth habit: A single female plant, vegetatively reproducing, a stoloniferous plant, which is short and very rapid spreading. Highly fibrous root system knits in most media within 3 to 5 weeks. In season, produces uniform, fine, relatively dense blades and holds its color for a greater time period than existing varieties of buffalograss. Becomes and remains dormant when supply of moisture is insufficient and rapidly revives with relatively small quantities of water.

Establishment rate (with irrigation):

*Sod.*—1-2 weeks.

*Plugs.*—8-12 weeks.

*Sprigs.*—12-16 weeks.

Regions of adaptation: Canadian border to central Mexico, optimum growth in Central Great Plains.

Blade:

*Shape.*—Long, slender.

*Length.*—About 10 cm to about 15 cm.

*Width.*—About 1.0 mm to about 1.8 mm; typically, 1.49 mm.

*Hairs.*—Abaxial only.

Mature plant height (without fertilization): About 10 cm to about 15 cm.

Internode:

*Length.*—At least about 15 to about 20 percent longer than existing cultivars of buffalograss; typically, 16.4 cm between the 2nd and 5th internodes.

*Diameter.*—Between the 4th and 5th internodes, about 0.75 cm to about 0.90 cm; typically, 0.86 cm.

Node pigmentation: Purple.

Stolon color: Midsummer; typically green 144A. Late fall; purplish typically, 65A.

Leaf color:

*Active (nondormant).*—Light green to blue green; typically, 143A.

*Dormant.*—Yellow to brown; typically, 161C.

Soils: Heavy clay, silty clay, loam, calcareous, neutral to alkaline pH.

Male inflorescence: Absent.

Comparative Data

The following tables provide data comparisons of selected morphologic, and growth characteristics between Prairie, Texoka and, in Table 7, Comanche buffalograsses. The letters following some of the numeral values appearing in the charts indicate significant distinctions in the particular characteristic of the two buffalograss varieties measured according to the Waller-Duncan Bayesian multiple comparison procedures. Torrie, J. H. *Principles and Procedures of Statistics: A biometric approach,* 190–191 (1980). The presence of a significant difference according to this method is indicated when the values in a column are followed by different letters.

TABLE 1

Color Ratings of Prairie in Comparison to Texoka Buffalograss established on May 17, 1988

| Cultivar | Date | Samples #1 | #2 | #3 |
|---|---|---|---|---|
| Prairie | 7/26/88 | 137b | 137c | 137c |
| | 2/1/89 | 161c | 164d | 161c |
| | 5/6/89 | 146b | 146b | 137c |
| Texoka | 7/26/88 | 137b | 137c | 137c |
| | 2/1/89 | 159b | 161d | 161d |
| | 5/6/89 | 147b | 137c | 147b |

TABLE 2

Coverage (% of area) of Prairie buffalograss in comparison to Texoka buffalograss

| Cultivar | Date of Observation 6/23/88 | 7/6/88 | 7/13/88 | 7/26/88 |
|---|---|---|---|---|
| Prairie | 21.0a* | 38.3a | 47.0a | 56.7a |
| Texoka | 12.3bc | 11.7c | 17.3bc | 21.0c |

| Cultivar | Date of Observation 8/4/88 | 3/23/89 | 4/8/89 |
|---|---|---|---|
| Prairie | 61.0a | 96.7a | 100a |
| Texoka | 27.7bc | 78.3ab | 85ab |

Vegetative plantings made 5/17/88 in the Coit Road Trials.

TABLE 3

Comparison of stolon production for Prairie and Texoka buffalograss at 7, 8, and 10 weeks after planting

| Cultivar | # Stolons 7 weeks | Longest Stolon (cm) 7 weeks | 8 weeks | 10 weeks |
|---|---|---|---|---|
| Prairie | 17.1a | 13.6a | 18.9a | 24.0a |
| Texoka | 4.1b | 6.3b | 12.3b | 16.3b |

Vegetative plantings made 5/17/88 in the Coit Road Trials.

TABLE 4

Relative frost tolerance of Prairie buffalograss compared to Texoka buffalograss following spring greenup and mid-March spring frost in the Coit Road Trials

| Cultivar | Frost Damage (1–9, 9 = no damage) |
|---|---|
| Prairie | 7.0a |
| Texoka | 3.0b |

Measurements of plants established on 5/17/88 made on 4-16-89.

TABLE 5

Quality performance of Prairie buffalograss as compared to Texoka buffalograss during the spring 1989 in Coit Road Trials

| Cultivar | 4/6/89 | 5/4/89 | 5/25/89 | 6/18/89 |
|---|---|---|---|---|
| Prairie | 6.0a | 7.3a | 7.0a | 8.0a |
| Texoka | 4.7b | 6.0b | 6.3b | 6.0b |

Vegetative planting was on 5/17/88.

TABLE 6

Components of turf quality* ratings of Prairie compared to Texoka

| Cultivar | Density (1–3)** | Uniformity (0–2)** | Smoothness (0–1)** | Color (0–2)** | Texture (0–1)** | Quality (1–9) |
|---|---|---|---|---|---|---|
| Prairie | 3.0a | 2.0a | 1.0a | 1.0 | 1.0 | 8.0a |
| Texoka | 1.8b | 0.5b | 0.0b | 0.0 | 1.0 | 3.3b |

Plants were vegetatively established in 1987 at the Linear Gradient Irrigation System field trials.

*Turf grass quality is based on uniformity, density of stand, texture of leaf width, growth habit of upright and prostrate stems, smoothness of surface and color. Beard, J. B. Turfgrass Science (1973)

**Rating scale.

TABLE 7

Comparative Study of Stolon Length, Leaf Blade Length, Leaf Blade Width, Sheath Length

| 1988 | Stolon Length-2–5* (cm) | Stolon Length-4–5** (cm) | Blade Length (cm) | Sheath Length (cm) | Leaf Width (mm) |
|---|---|---|---|---|---|
| Prairie | 163.70 | 56.7 | 11.08 | 12.83 | 1.49 |
| Texoka | 128.79 | 49.89 | 17.57 | 17.36 | 1.50 |
| Comanche | 110.23 | 37.37 | 15.08 | 14.55 | 1.46 |

*Length of stolon between internodes 2 to 5.

**Length of stolon between internodes 4 to 5.

TABLE 8

| Morphological Description | Prairie | Comanche |
|---|---|---|
| A. Vegetative Traits. | | |
| (P = present, A = absent) | | |
| 1. STOLONS | P | P |
| a. Color or pigmentation (juvenile growth) 1 = White, 2 = Purple | 2 | — |
| b. Internode Length (mm) (2nd-5th) | 164 | 110 |
| c. Internode Diameter maximum (mm) (between 4th-5th) | .86 | .81 |
| 2. NODES | | |
| a. Color or pigmentation (juvenile growth) 1 = White, 2 = Purple or Color Chart | 2 | — |
| 3. RHIZOMES (P = present, A = absent) | A | A |
| 4. LEAF BLADE: | | |
| a. Color: Color Chart | | |
| (1) Dormant | 161C | — |
| (2) Active (non-dormant) | 143A | 137C |
| b. Dimensions | | |
| (1) Width (mm) (3rd or 4th leaf below apical meristem) | 1.49 | 1.46 |
| (2) Length (mm) | 11.1 | 15.1 |
| c. Hairiness: 1 = glabrous 2 = pubescent | | |
| (1) Abaxial | 2 (slight) | 1 |
| (2) Adaxial | 1 | 1 |
| 5. SHEATH (Adaxial margin): | | |
| a. Hairs: 1 = Absent 2 = Present, (L = long S = short) | 2L | 1 |
| b. Length (mm) | 12.8 | 14.6 |
| 6. COLLAR (Adaxial margin): Hairness: 1 = glaborous 2 = pubescent | 2L | 1 |
| b. Floral Traits. | | |
| (P = present, A = absent) | | |
| 1. MALE INFLORESCENCE | A | P |
| 2. FEMALE INFLORESCENCE | P | P |
| a. Stigma color: 1 = White, 2 = Purple | 2 | — |
| b. Spikelet: | | |
| (1) Number of burrs/sp | 1.9 | 1.4 |
| (2) Burr length (mm) | 8.1 | 6.6 |
| (3) Burr width (mm) | 3.6 | 3.8 |
| (4) # Flwrs per Burr | 2.6 | 2.4 |

TABLE 8-continued

| Morphological Description | Texoka |
|---|---|
| A. Vegetative Traits. | |
| (P = present, A = absent) | |
| 1. STOLONS | P |
| a. Color or pigmentation (juvenile growth) 1 = White, 2 = Purple | 2 |
| b. Internode Length (mm) (2nd-5th) | 129 |
| c. Internode Diameter maximum (mm) (between 4th-5th) | .95 |
| 2. NODES | |
| a. Color or pigmentation (juvenile growth) 1 = White, 2 = Purple or Color Chart | Variable |
| 3. RHIZOMES (P = present, A = absent) | A |
| 4. LEAF BLADE: | |
| a. Color: Color Chart | |
| (1) Dormant | 161D |
| (2) Active (non-dormant) | 143A |
| b. Dimensions | |
| (1) Width (mm) (3rd or 4th leaf below apical meristem) | 1.50 |
| (2) Length (mm) | 17.6 |
| c. Hairiness: 1 = glabrous 2 = pubescent | |
| (1) Abaxial | 2 |
| (2) Adaxial | 2 |
| 5. SHEATH (Adaxial margin): | |
| a. Hairs: 1 = Absent 2 = Present, (L = long S = short) | 2S |
| b. Length (mm) | 17.4 |
| 6. COLLAR (Adaxial margin): Hairness: 1 = glaborous 2 = pubescent | 2S |
| b. Floral Traits. | |
| (P = present, A = absent) | |
| 1. MALE INFLORESCENCE | P |
| 2. FEMALE INFLORESCENCE | P |
| a. Stigma color: 1 = White, 2 = Purple | 2 |
| b. Spikelet: | |
| (1) Number of burrs/sp | 1.8 |
| (2) Burr length (mm) | 7.3 |
| (3) Burr width (mm) | 3.8 |
| (4) # Flwrs per Burr | 2.7 |

TABLE 9

Relative Performance of Prairie in Comparison to Other Varieties for the Following Characteristics.

| CHARACTER (1-9 scale, 9 = best, 0 = not tested) | Prairie | Comanche | Texoka |
|---|---|---|---|
| Rate of Spread | 9 | 3 | 5 |
| Turf Density | 7 | 3 | 3 |
| Drought tolerance | 9 | 0 | 6 |
| Injury regrowth potential | 7 | 0 | 0 |
| Shade tolerance | 3 | 3 | 3 |
| Color | 4 | 5 | 6 |
| Cold Tolerance | 7 | 7 | 7 |
| Heat Tolerance | 9 | 7 | 7 |
| Salinity Tolerance | 3 | 0 | 3 |

What is claimed:

1. A new and distinct perennial buffalograss cultivar having 2n=40 chromosomes, substantially as herein shown and described, distinguished by rapidly spreading stolons, competitive growth, short height, durability, frost and drought tolerance, low maintenance requirements, uniform height, color and density, and improved turf performance.

* * * * *

UNITED STATES PATENT AND TRADEMARK OFFICE

CERTIFICATE OF CORRECTION

PATENT NO. : Plant 7,539

DATED : May 28, 1991

INVENTOR(S) : Engelke et al.

It is certified that error appears in the above-indentified patent and that said Letters Patent is hereby corrected as shown below:

Column 2, line 29, after "has", insert -- a --.

Column 6, line 47 (Table 6), after (1-9), insert --**--.

Column 6, line 54, change "Turfgrass Science" to

--Turfgrass Science--.

Signed and Sealed this

Fourth Day of January, 1994

*Attest:*

*Attesting Officer*

BRUCE LEHMAN

*Commissioner of Patents and Trademarks*